(12) United States Patent
Wissel et al.

(10) Patent No.: US 11,484,286 B2
(45) Date of Patent: Nov. 1, 2022

(54) ULTRASOUND EVALUATION OF ANATOMICAL FEATURES

(71) Applicant: KONINKLIJKE PHILIPS N.V., Eindhoven (NL)

(72) Inventors: Tobias Wissel, Lübeck (DE); Irina Waechter-Stehle, Hamburg (DE); Frank Michael Weber, Hamburg (DE); Arne Ewald, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 419 days.

(21) Appl. No.: 16/477,796

(22) PCT Filed: Feb. 12, 2018

(86) PCT No.: PCT/EP2018/053400
§ 371 (c)(1),
(2) Date: Jul. 12, 2019

(87) PCT Pub. No.: WO2018/146296
PCT Pub. Date: Aug. 16, 2018

(65) Prior Publication Data
US 2019/0374194 A1    Dec. 12, 2019

(30) Foreign Application Priority Data
Feb. 13, 2017  (EP) .................................. 17155776

(51) Int. Cl.
*A61B 8/08*  (2006.01)
*A61B 8/06*  (2006.01)
(Continued)

(52) U.S. Cl.
CPC .............. *A61B 8/0883* (2013.01); *A61B 8/06* (2013.01); *A61B 8/14* (2013.01); *A61B 8/462* (2013.01);
(Continued)

(58) Field of Classification Search
CPC ........... A61B 8/0883; A61B 8/06; A61B 8/14; A61B 8/462; A61B 8/488; A61B 8/5238;
(Continued)

(56) References Cited

U.S. PATENT DOCUMENTS 6,063,030 A    5/2000  Vara et al.
6,261,234 B1   7/2001  Lin
(Continued)

FOREIGN PATENT DOCUMENTS

CN    103455710 A    12/2013
WO    2005078666 A1    8/2005
(Continued)

OTHER PUBLICATIONS

International Search Report and Written Opinion for International Application No. PCT/EP2018/053400, filed Feb. 12, 2018, 14 pages.
(Continued)

*Primary Examiner* — Rochelle D Turchen

(57) ABSTRACT

An ultrasound image processing apparatus (10) is disclosed comprising a processor arrangement (16) adapted to map a model (1) of an anatomical feature of interest onto an ultrasound image showing at least a section of said anatomical feature of interest and to segment said ultrasound image in accordance with the mapped model; and a touchscreen display (18, 19) adapted to display said ultrasound image including the mapped anatomical model. The processor arrangement is responsive to the touchscreen display and adapted to recognize a type of a user touch motion (3) provided through the touchscreen display (18, 19), each type of user touch motion being associated with a particular type of alteration of said mapping and alter said mapping in accordance with the recognized type of user touch motion. Also disclosed are an ultrasound imaging system, a com-
(Continued)

puter-implemented method and a computer program product.

18 Claims, 10 Drawing Sheets

(51) Int. Cl.
  *A61B 8/14* (2006.01)
  *A61B 8/00* (2006.01)
  *G16H 40/63* (2018.01)
  *G06F 3/04883* (2022.01)
  *G06T 19/00* (2011.01)
  *G06T 19/20* (2011.01)

(52) U.S. Cl.
  CPC ......... *A61B 8/488* (2013.01); *A61B 8/5238* (2013.01); *A61B 8/0866* (2013.01); *A61B 8/4427* (2013.01); *A61B 8/463* (2013.01); *A61B 8/467* (2013.01); *A61B 8/483* (2013.01); *G06F 3/04883* (2013.01); *G06F 2203/04808* (2013.01); *G06T 19/006* (2013.01); *G06T 19/20* (2013.01); *G06T 2200/24* (2013.01); *G06T 2210/41* (2013.01); *G06T 2219/2016* (2013.01); *G16H 40/63* (2018.01)

(58) Field of Classification Search
  CPC ..... A61B 8/0866; A61B 8/4427; A61B 8/463; A61B 8/467; A61B 8/483; G06F 3/04883; G06F 2203/04808; G06T 19/006; G06T 19/20; G06T 2200/24; G06T 2210/41; G06T 2219/2016; G16H 40/63
  See application file for complete search history.

(56) References Cited

U.S. PATENT DOCUMENTS

| | | |
|---|---|---|
| 2003/0195418 A1 | 10/2003 | Barnes et al. |
| 2005/0238233 A1 | 10/2005 | Mulet Parada et al. |
| 2008/0267468 A1 | 10/2008 | Geiger et al. |
| 2009/0043195 A1 | 2/2009 | Poland |
| 2010/0125196 A1 | 5/2010 | Park et al. |
| 2010/0179427 A1 | 7/2010 | Yamamoto |
| 2013/0041243 A1* | 2/2013 | Byrd ............... A61B 90/37 600/374 |
| 2013/0121549 A1* | 5/2013 | Pekar ............... G06V 10/26 382/128 |
| 2013/0324850 A1 | 12/2013 | Petruzzelli et al. |
| 2014/0098049 A1 | 4/2014 | Koch et al. |
| 2014/0181717 A1 | 6/2014 | Lahti et al. |
| 2015/0265247 A1 | 9/2015 | Roh et al. |
| 2016/0005166 A1* | 1/2016 | Xu ............... G06T 7/12 382/128 |
| 2016/0081659 A1 | 3/2016 | Perrey et al. |
| 2016/0124618 A1* | 5/2016 | Bostick ............ G06F 3/0481 715/790 |
| 2016/0228091 A1 | 8/2016 | Chiang et al. |
| 2017/0296149 A1 | 10/2017 | Kobayashi et al. |

FOREIGN PATENT DOCUMENTS

| | | |
|---|---|---|
| WO | 2015011256 A1 | 1/2015 |
| WO | 2015048327 A2 | 4/2015 |
| WO | 2016052355 A1 | 4/2015 |

OTHER PUBLICATIONS

Ecabert, et al., "Automatic Model-Based Segmentation of the Heart in CT Images Medical Imaging", IEEE Transactions on Medical Imaging, Sep. 2008, vol. 27, Issue 9, pp. 1189-1201. (Abstract).

* cited by examiner

ULTRASOUND EVALUATION OF ANATOMICAL FEATURES

RELATED APPLICATIONS

This application is the U.S. National Phase application under 35 U.S.C. § 371 of International Application No. PCT/EP2018/053400, filed on Feb. 12, 2018, which claims the benefit of European Application No. 17155776.2, filed Feb. 13, 2017. This application is hereby incorporated by reference herein.

FIELD OF THE INVENTION

The present invention relates to ultrasound image processing apparatus comprising a processor arrangement adapted to map a model of an anatomical feature of interest onto an ultrasound image showing at least a cross-section of said anatomical feature of interest and to segment said ultrasound image in accordance with the mapped model.

The present invention further relates to an ultrasound imaging system comprising such an ultrasound image processing apparatus.

The present invention further relates to a computer-implemented method for mapping a model of an anatomical feature of interest onto an ultrasound image showing at least a cross-section of said anatomical feature of interest and segmenting said ultrasound image in accordance with the mapped model.

The present invention further relates to a computer program product for implementing such a computer-implemented method.

BACKGROUND OF THE INVENTION

Ultrasound plays an essential role in many diagnostic imaging techniques including but not limited to cardiovascular imaging. In this context, diagnosis and treatment planning typically rely on a clear delineation of relevant anatomical sites such as the ventricles, the atria or surrounding vessels in the cardiac ultrasound images in order to facilitate meaningful evaluation of the heart under investigation. Historically, measurements (of the volume) of cardiac chambers, such as the left ventricle, have been generated by a user hand-tracing the endocardial boundary of the chamber. Such tracings are subject to significant variability due to differences in the criteria different users utilize in determining where to locate the tracing.

In order to address such unwanted variability, this evaluation process has been automated by using anatomically intelligent model-based segmentation, where generic, shape-constrained heart models are fitted to the imaging data. For example, such a heart model is disclosed in WO 2016/142204 A1. The heart model may be subsequently used as an aid to subject the mapped cardiac structure in the ultrasound imagery to segmentation algorithms in order to obtain the dimensions of interest of the cardiac anatomical sites under investigation, e.g. by mapping such a model onto a volumetric image. A suitable segmentation algorithm is disclosed by O. Ecabert et al. in "Automatic Model-Based Segmentation of the Heart in CT Images", IEEE Transactions on Medical Imaging, 2008 (27), pages 1189-1201.

The success of the segmentation algorithm requires an accurate placement of the heart model within the imaging data, e.g. a volumetric image. While this placement generally includes basic coordinate transformations such as rotation, translation and scaling, further processing also involves affine transformations of single model components (e.g. ventricles or atria) or the selection from a set of mean shapes representing different heart pathologies (e.g. dilated or normal shape). In some cases, parts of this automatic placement process fail, for example, due to poor ultrasound image quality or a limited field-of-view (FoV) within the ultrasound imagery.

Two typical examples are shown in FIG. 1 and FIG. 2. In FIG. 1, due to the imaging data showing a heart of rather small size, the automatic placement of the heart model 1 including left ventricle (LV), right ventricle (RV), left atrium (LA) and right atrium (RA) anatomical site models failed by misjudgment of the overall model scale, causing the entire heart to be wrapped by the left ventricle model of the heart model 1. In FIG. 2, the ultrasound imaging data exhibits a limited field of view in combination with rather poor imaging contrast, particularly at the apex. Consequently, the translation parameter was misjudged by the automatic process of the placement of the heart model 1 within the imaging data, such that the actual right ventricle is covered by the left side of the heart model 1.

In case of such placement failures of the heart model 1, the analysis pipeline cannot be performed unless the user manually places the heart model 1 in the correct position within the ultrasound image, which can be tedious and time-consuming. This for example is disclosed in WO 2005/078666 A1. As will be readily understood by the skilled person, such model placement problems are not limited to heart models but equally apply to placement of models of other anatomical features of interest, e.g. organ models, fetal models and so on.

SUMMARY OF THE INVENTION

The present invention seeks to provide an ultrasound imaging processing apparatus that allows a user to more easily align a heart model with a captured ultrasound image comprising at least a section of an anatomical feature of interest, such as a patient's heart.

The present invention further seeks to provide an ultrasound imaging system comprising such an ultrasound image processing apparatus.

The present invention further seeks to provide a computer-implemented method that allows a user to more easily align a heart model with a captured ultrasound image comprising at least a section of an anatomical feature of interest such as a patient's heart.

The present invention further seeks to provide a computer program product for implementing such a method on an ultrasound imaging processing apparatus.

According to an aspect, there is provided an ultrasound image processing apparatus comprising a processor arrangement adapted to map a model of an anatomical feature of interest onto an ultrasound image showing at least a section of said anatomical feature of interest of a patient and to segment said ultrasound image in accordance with the mapped model; and a touchscreen display adapted to display said ultrasound image including the mapped model; wherein the processor arrangement is responsive to the touchscreen display and adapted to recognize a type of user touch motion from a plurality of types of user touch motions provided through the touchscreen display, each type of user touch motion being associated with a particular alteration of said mapping; and alter said mapping in accordance with the recognized type of user touch motion. The use of touch interaction with a touchscreen display displaying the ultrasound image and the anatomical model overlaying this image provides the user with an intuitive and straightforward manner in which an incorrectly positioned anatomical model can be adjusted to its correct position according to the user, thereby providing a user-friendly ultrasound image processing apparatus that facilitates efficient adjustment of incorrectly positioned anatomical models following the automatic positioning thereof. In preferred embodiments, the anatomical model is mapped onto a volumetric (3D) ultrasound image in which a substantial part of the anatomical feature of interest or the entire anatomical feature of interest is imaged, although it should be understood that in alternative embodiments such models may be mapped onto a 2-D ultrasound image, e.g. an image slice from a volumetric image or an image slice from a sequence of 2-D images captured along a scanning direction.

The processor arrangement may be further adapted to segment said ultrasound image in accordance with the altered mapped model such that the user corrections lead to improved automatically generated parametric measurements of the patient's anatomical feature as obtained by the segmentation algorithms.

In embodiments in which the model comprises a plurality of anatomical components, the processor arrangement may be adapted to select or deselect one of said anatomical components in response to a user interaction with a region of the touchscreen display displaying said anatomical component such as to limit the application of subsequent gestures to a selected component or terminate such limiting in case of the deselection of the component. To this end, the processor arrangement preferably is further adapted to alter the mapping of said selected anatomical component in response to a further user touch instruction provided through the touchscreen display.

In embodiments in which the anatomical model is configurable, the processor arrangement may be adapted to select a configuration of the model in response to a swiping motion provided by the user on the touchscreen display, thereby allowing the user to select an appropriate model, e.g. a dilated heart model, a normal heart model or the like, in a straightforward manner. Other types of user commands provided on the touchscreen to invoke the aforementioned manipulations of the anatomical model are of course equally feasible.

The ultrasound image processing apparatus may be a workstation or alternatively may be a portable ultrasound image processing apparatus such as a tablet computer.

According to another aspect, there is provided an ultrasound imaging system comprising the ultrasound image processing apparatus of any of the herein described embodiments and an ultrasound probe for providing the ultrasound image to said apparatus. Such an ultrasound imaging system facilitates accurate determination of anatomical and/or parametric measurements by the provision of ultrasound images to the ultrasound image processing apparatus as described above.

According to another aspect, there is provided a computer-implemented method of extracting parametric measurements from an ultrasound image showing at least a section of a patient's anatomical feature of interest, the method comprising mapping a model of the anatomical feature of interest onto the ultrasound image; receiving a type of user touch motion from a plurality of types of user touch motions from a touchscreen display, each type of user touch motion being associated with a particular alteration of said mapping; recognizing said type of user touch motion; altering said mapping in accordance with the recognized type of user touch motion; and segmenting the ultrasound image in accordance with the altered mapped model to extract said parametric measurements. Such a method enables a user of an ultrasound image processing apparatus implementing the method to correct positioning errors of the anatomical model on the ultrasound image in an intuitive and straightforward manner, thereby providing an improved user experience. Moreover, such motion can be directly translated into an intended transformation of the anatomical model.

The method may further comprise displaying the extracted parametric measurements on the touchscreen display to provide to the user with such measurements.

In embodiments in which the model comprises a plurality of anatomical components, the method may further comprise selecting or deselecting one of said anatomical components in response to a user interaction with a region of the touchscreen display displaying said anatomical component such as to limit the application of subsequent gestures to a selected component or terminate such limiting in case of the deselection of the component. To this end, the method may be further adapted to alter the mapping of said selected anatomical component in response to a further user touch instruction provided through the touchscreen display.

In embodiments in which the model is configurable, the method may further comprise selecting a configuration of the model in response to a swiping motion provided by the user on the touchscreen display, thereby allowing the user to select an appropriate model, e.g. a dilated heart model, a normal heart model or the like, in a straightforward manner.

It is reiterated that other types of user commands provided on the touchscreen to invoke the aforementioned manipulations of the anatomical model are of course equally feasible.

According to yet another aspect, there is provided a computer program product comprising a computer readable storage medium having computer readable program instructions embodied therewith for, when executed on a processor arrangement of an ultrasound image processing apparatus of any of the herein described embodiments, cause the processor arrangement to implement the method according to any of the herein described embodiments. Such a computer program product for example may be used to enhance existing ultrasound image processing apparatuses by installation of the computer readable program instructions thereon.

BRIEF DESCRIPTION OF THE DRAWINGS

Embodiments of the invention are described in more detail and by way of non-limiting examples with reference to the accompanying drawings, wherein.

DETAILED DESCRIPTION OF EMBODIMENTS

Figure 1:
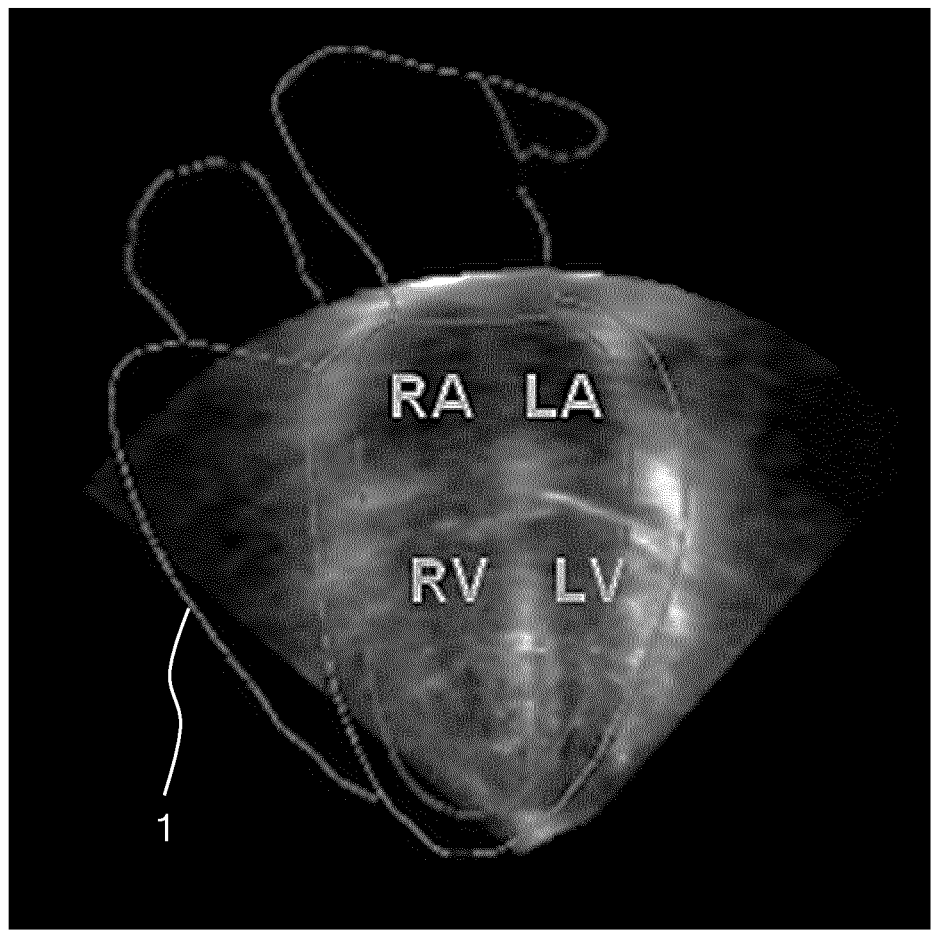
FIG. 1 is an image of an incorrectly mapped heart model onto a cardiac ultrasound image.

It should be understood that the Figures are merely schematic and are not drawn to scale. It should also be understood that the same reference numerals are used throughout the Figures to indicate the same or similar parts.

Figure 3:
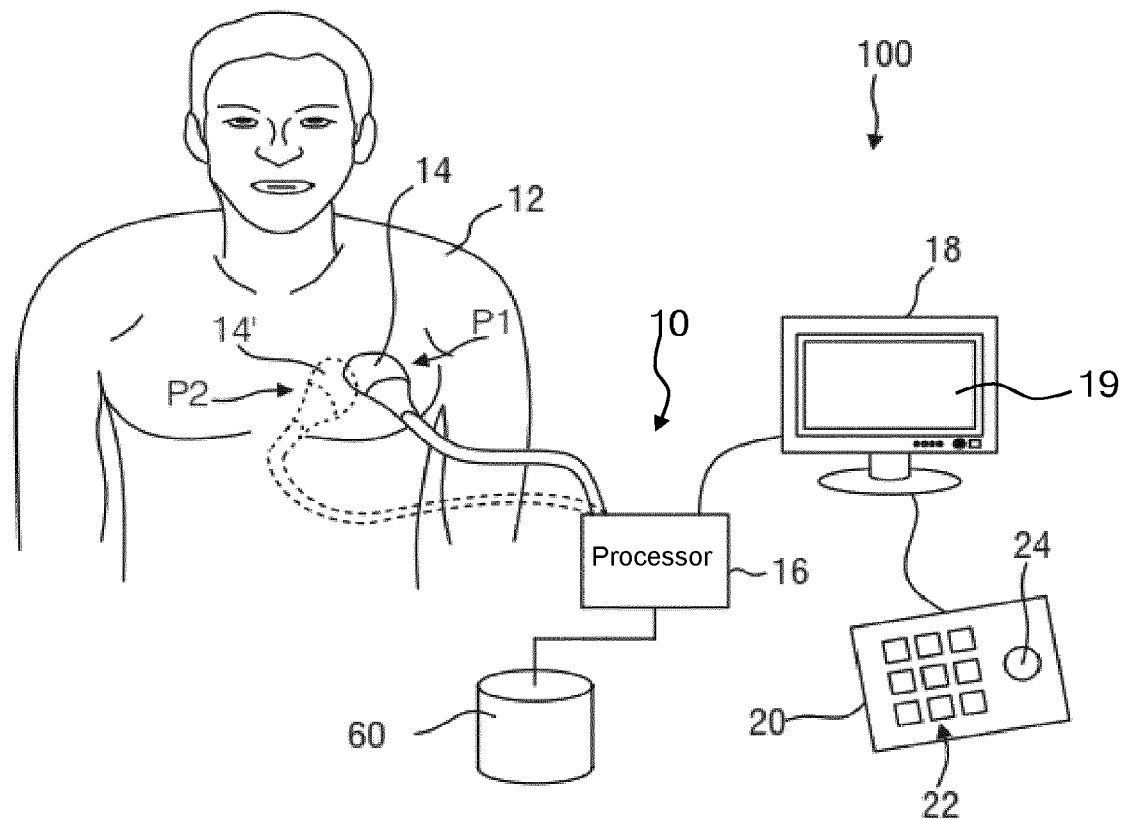
FIG. 3 shows a schematic representation of an ultrasound imaging system in use to scan a part of a patients body.

FIG. 3 shows a schematic illustration of an ultrasound system 100, in particular a medical two-dimensional (2-D) or three-dimensional (3-D) ultrasound imaging system. The ultrasound system 100 may be applied to inspect a volume of an anatomical site, in particular an anatomical site of a patient 12, such as the patient's heart. This for example may involve monitoring the anatomical site over a period of time to track progress of a condition affecting the anatomical site. The ultrasound system 100 comprises an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. Such an ultrasound probe 14 may be a probe to be applied to a skin portion, e.g. in the chest region, of the patient 12 or alternatively may be a transesophageal echocardiography probe. The transducer elements may be arranged in a one-dimensional array, e.g. in case of 2-D medical imaging, or in a two-dimensional array, in particular for providing a multi-planar or three-dimensional image in case of a 3-D ultrasound system 100. A particular example for a three-dimensional ultrasound system which may be the CX40 Compact Xtreme ultrasound system sold by the applicant, in particular together with a X6-1 or X7-2t TEE transducer of the applicant or another transducer using the xMatrix technology of the applicant. In general, matrix transducer systems as found on Philips iE33 systems or mechanical 3D/4D transducer technology as found, for example, on the Philips iU22 and HD15 systems may be applied in conjunction with the current invention.

The ultrasound probe 14 is typically communicatively coupled to an ultrasound image processing apparatus 10, which coupling may be achieved in any suitable manner, e.g. a wireless coupling or a wired coupling such as through a coaxial cable, through which control instructions for the ultrasound probe 14 may be provided by the ultrasound image processing apparatus 10. Such an ultrasound image processing apparatus 10 may take any suitable shape, such as a dedicated workstation or console of the ultrasound imaging system 100 or alternatively may be a general-purpose computing device, e.g. a personal computer, laptop computer or tablet computer on which a computer program product is installed that configures the computing device to be operable as the ultrasound image processing apparatus 10.

The ultrasound image processing apparatus 10 may comprise a processor arrangement 16 including an image reconstruction unit that controls the provision of a 2-D or 3-D image sequence via the ultrasound system 100. As will be explained in further detail below, the image reconstruction unit may control not only the acquisition of data via the transducer array of the ultrasound probe 14, but also signal and image processing that form the 2-D or 3-D image sequence out of the echoes of the ultrasound beams received by the transducer array of the ultrasound probe 14.

The ultrasound system 100 may further comprise a display device 18 (from here on also referred to as display 18) for displaying the 2-D or 3-D image or image sequence to the user. The display 18 may form an integral part of or may be communicatively coupled to the ultrasound image processing apparatus 10. The display 18 comprises a touchscreen 19 through which a user may interact with image data displayed thereon, e.g. displayed 2-D images 2-D slices of a 3-D volumetric ultrasound image, or, preferably, a volume rendered display image of the volumetric ultrasound image of an anatomical region of interest of the patient 12, such as the patient's heart in some embodiments of the present invention, as will be explained in further detail below. Any suitable type of touchscreen 19 may be used in the display 18.

Still further, an input device 20 may be provided that may comprise a user interface 22 such as a keyboard and further inputting devices, for example a trackball 24. The input device 20 might be connected to the display 18 or directly to the processor arrangement 16. The ultrasound system 100 may further comprise a data storage arrangement 60, e.g. one or more memory devices, hard disks, optical discs, or the like, in which the processor arrangement 16 or the image reconstruction unit may store image frames and image frame processing data, e.g. for evaluation at a later date, i.e. upon completion of the ultrasound image data acquisition.

Figure 4:
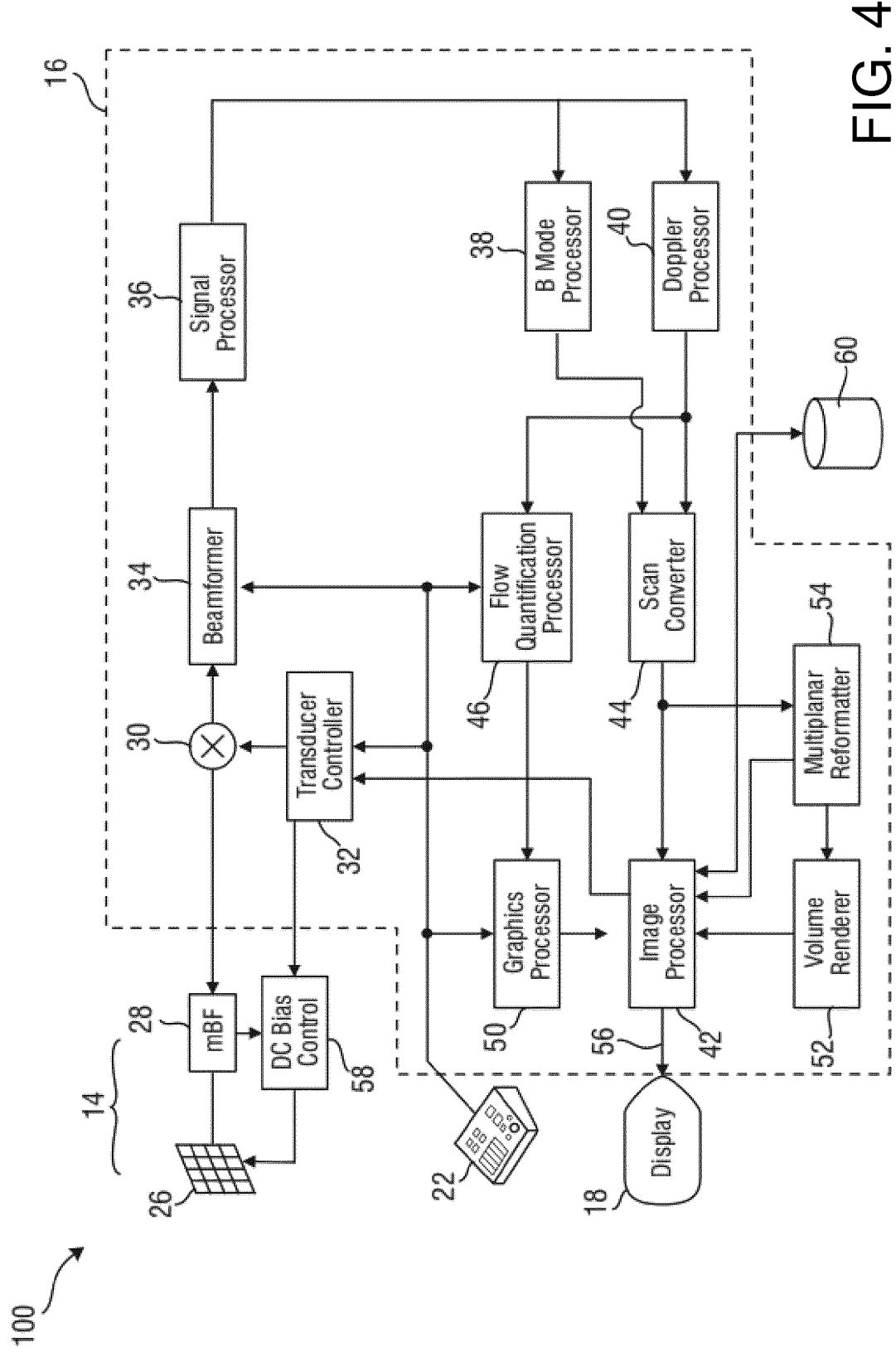
FIG. 4 shows a schematic block diagram of an embodiment of an ultrasound imaging system with an array transducer.

FIG. 4 illustrates a schematic block diagram of the ultrasound system 100 including the processor arrangement 16 of the ultrasound image processing apparatus 10. The ultrasound probe 14 may, for example, comprise a CMUT transducer array 26. The transducer array 26 may alternatively comprise piezoelectric transducer elements formed of materials such as PZT or PVDF. The transducer array 26 is a one- or a two-dimensional array of transducer elements capable of scanning in two dimensions for 2D imaging or in three dimensions for 3D imaging. The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.).

The microbeamformer 28 may be coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34. The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for the array of transducer cells. The DC bias control 58 sets DC bias voltage(s) that are applied to the transducer cells, e.g. CMUT cells.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36, which may form part of the aforementioned processor arrangement 16. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.)

The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue.

The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format, or a pyramidal three dimensional (3D) image. The scan converter 44 can overlay a B mode structural image with colors corresponding to motion at points in the image field with their Doppler-estimated velocities to produce a color Doppler image which depicts the motion of tissue and blood flow in the image field.

In a 3-D imaging system, the multiplanar reformatter 54 will convert echoes which are received from points in a common plane in a volumetric region of the body into an ultrasonic image of that plane, as described in U.S. Pat. No. 6,443,896 (Detmer). A volume renderer 52 converts the echo signals of a 3D data set into a projected 3D image sequence 56 over time as viewed from a given reference point as described in U.S. Pat. No. 6,530,885 (Entrekin et al.). The 3-D image sequence 56 is transferred from the scan converter 44, multiplanar reformatter 54, and volume renderer 52 to an image processor 42 for further enhancement, buffering and temporary storage for display on the display 18.

The image processor 42 for example may be adapted to map the heart model 1 to a cardiac ultrasound image, e.g. a 2-D image or preferably a 3-D volumetric ultrasound image (or a user-selected slice thereof), and to segment the cardiac ultrasound image in accordance with any suitable segmentation algorithm, e.g. a segmentation algorithm forming part of a segmentation software module executed by the image processor 42. At this point, it should be understood that reference to the image processor 42 is intended to also cover implementations of the ultrasound image processing apparatus 10 in which the functionality of the image processor 42 is provided by a plurality of cooperating processors. For example, in such implementations, a dedicated heart model mapping processor and a dedicated segmentation processor may cooperate to implement the functionality of the image processor 42.

In addition to being used for imaging, the blood flow values produced by the Doppler processor 40 and tissue structure information produced by the B mode processor 38 may be transferred to a quantification processor 46 forming part of the processor arrangement. This quantification processor 46 may produce measures of different flow conditions such as the volume rate of blood flow as well as structural measurements such as the sizes of organs and gestational age. The quantification processor 46 may receive input from the user interface 22, such as the point in the anatomy of an image where a measurement is to be made.

Output data from the quantification processor 46 may be transferred to a graphics processor 50 forming part of the processor arrangement for the reproduction of measurement graphics and values with the image on the display 18. The graphics processor 50 can also generate graphic overlays for display with the ultrasound images, such as the overlay of the heart model 1 over a cardiac ultrasound image to which the heart model 1 is mapped. These graphic overlays can further contain standard identifying information such as patient name, date and time of the image, imaging parameters, and the like. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system. The user interface 22 may also be coupled to the multiplanar reformatter 54 for selection and control of the planes of multiple multiplanar reformatted (MPR) images which may be used to perform quantified measures in the image field of the MPR images in case of a 3D imaging system.

The quantification processor 46 may be further arranged to receive user touch instructions through the touchscreen 19 for adjusting the mapping of the heart model 1 to the cardiac ultrasound image displayed on the display 18 as will be explained in further detail below. The quantification processor 46 may interpret the received user touch instructions to extract an adjustment of the mapping of the heart model 1 from the received user touch instruction and relay this adjustment to the image processor 42. Typically, such adjustments are referenced to the current view plane of a volumetric image displayed on the display 18 in case of such a volumetric image being utilized. The image processor 42 may be adapted to adjust the automated mapping of the heart model 1 to the cardiac ultrasound image accordingly and to perform the segmentation of the cardiac ultrasound image in accordance with the remapped heart model 1.

Alternatively, the image processor 42 may be responsive to the touchscreen 19 and may be adapted to interpret user touch instructions provided through the touchscreen 19 in order to adjust the mapping of the heart model 1 in accordance with the interpreted user touch instructions, thereby bypassing the quantification processor 46. It should be understood that other processor arrangements of the ultrasound image processing apparatus 10 for interpreting such user touch instructions provided through the touchscreen 19 and for remapping the heart model 1 in accordance with the interpreted user touch instructions and performing the segmentation of the cardiac ultrasound image in accordance with the remapped heart model may be contemplated and will be immediately apparent to the skilled person.

It is reiterated that the aforementioned ultrasound system 100 has only been explained as one possible example for an application of the medical ultrasound image processing apparatus 10. It shall be noted that the aforementioned ultrasound system 100 does not have to comprise all of the components explained before. On the other hand, the ultrasound system 100 may also comprise further components, if necessary. Still further, it shall be noted that a plurality of the aforementioned components does not necessarily have to be realized as hardware, but may also be realized as software components. A plurality of the aforementioned components may also be comprised in common entities or even in one single entity and do not all have to be realized as separate entities, as this is schematically shown in FIG. 3.

As previously explained, the ultrasound image processing apparatus 10 is configured to automatically map the heart model 1 including LV, RV, LA and RA anatomical site models onto an ultrasound image, preferably a volumetric ultrasound image, comprising an image of the heart of the patient 12, typically but not necessarily a cross-sectional view of the patient's heart, for example using the mapping algorithms disclosed in WO 2016/142204 A1. Such a heart model typically is a model-based segmentation algorithm utilizing prior knowledge with regard to the general structural layout of the heart, how the heart location varies within 3-D volumetric ultrasound images, how the heart shape varies between different patients and the ways in which the heart is imaged using ultrasound imaging. As such heart models are well-known per se, the heart model 1 will not be described in further detail for the sake of brevity only. It suffices to say that any suitable heart model may be used as the heart model 1.

Such mapping is typically followed by the automatic segmentation of the ultrasound image with the mapped heart model 1 in order to automatically obtain measurements of the heart, e.g. measurement of parameters such as ejection fraction and cardiac output, which require the volume of blood in a heart chamber at various phases of the heart cycle to be delineated in two or three dimensional images of a heart chamber.

Figure 2:
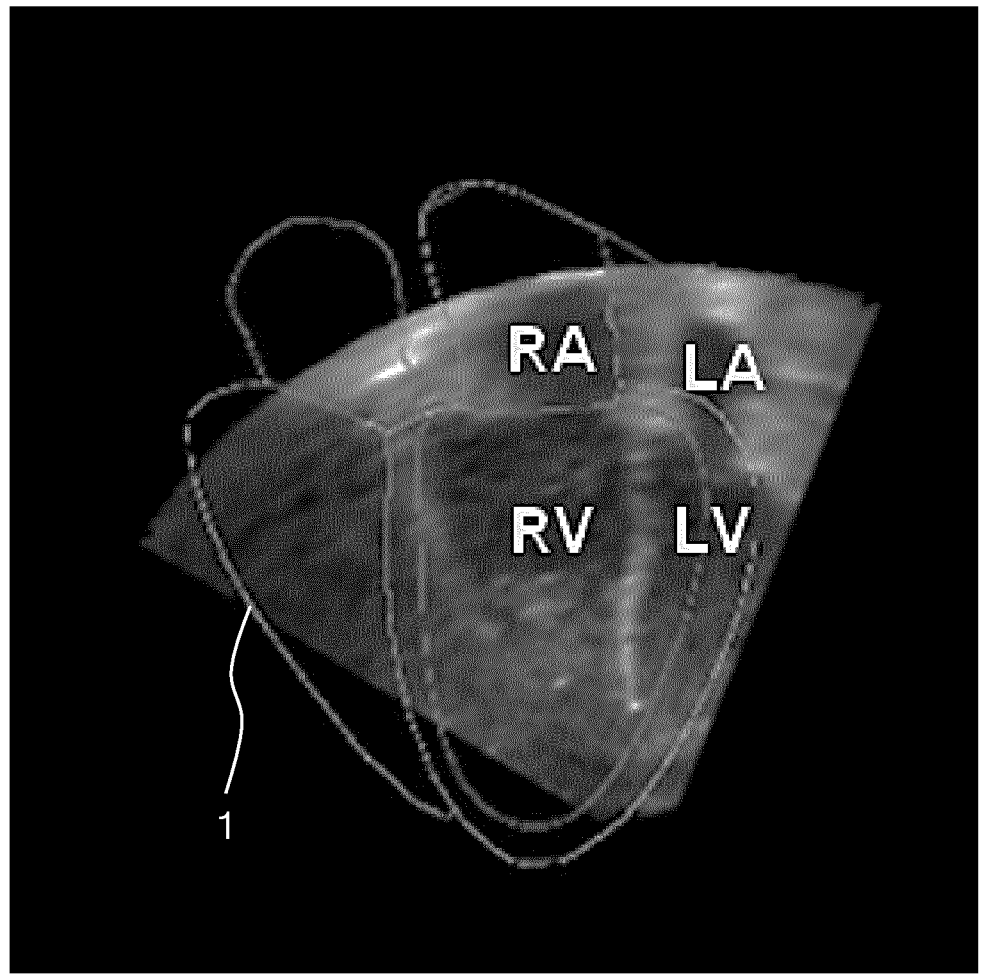
FIG. 2 is an image of an incorrectly mapped heart model onto another cardiac ultrasound image.

However, as explained above in more detail with the aid of FIG. 1 and FIG. 2, the mapping algorithm deployed by the heart model 1 to map itself onto the ultrasound image of the patient's heart is not always successful, such that subsequent segmentation of the ultrasound image in accordance with the mapped heart model 1 will generate meaningless results. In such scenarios, it is necessary for the user of the ultrasound image processing apparatus 10 to manually reposition the heart model 1 relative to the ultrasound image prior to the execution of the segmentation algorithms to ensure that the measurements obtained with the segmentation algorithms are clinically relevant, i.e. meaningful.

Figure 5:
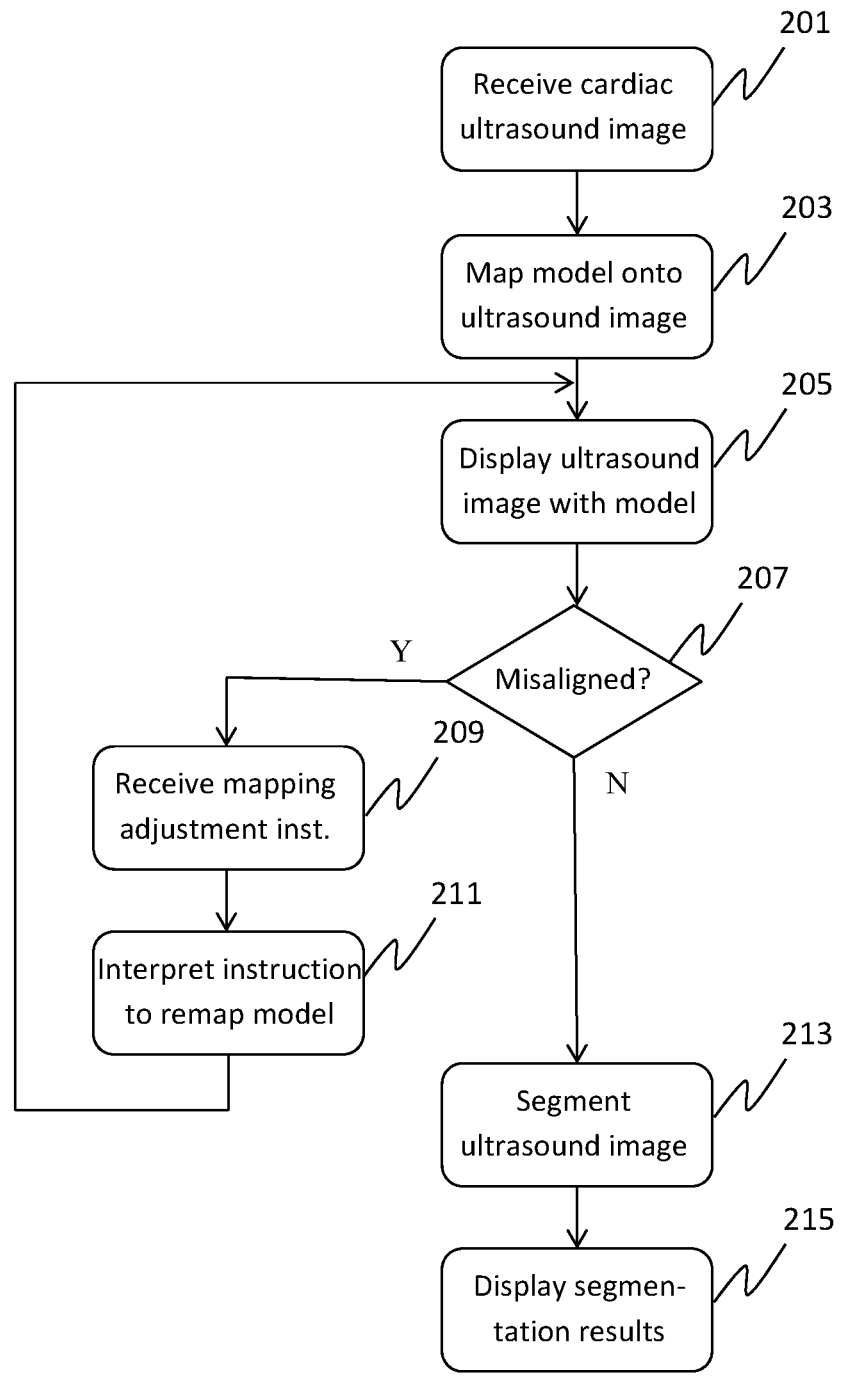
FIG. 5 is a flowchart of an example embodiment of a computer-implemented method according to the present invention.

In accordance with embodiments of the present invention, the ultrasound image processing apparatus 10 is configured to implement the method 200, a flow chart of which is depicted in FIG. 5. To this end, the processor arrangement 16 of the ultrasound image processing apparatus 10 may be adapted to implement the various operations of the method 200, some of which have already been described above. In accordance with this method 200, a user of the ultrasound image processing apparatus 10 can provide touch instructions through the touchscreen 19 of the display 18, which touchscreen instructions are interpreted by the processor arrangement 16 as mapping adjustment instructions for the automated mapping of the heart model 1 on a cardiac ultrasound image.

To this end, the method 200 starts in 201 with receiving a captured cardiac ultrasound image, e.g. a cardiac ultrasound image retrieved from the data storage arrangement 60 in response to a user selection signal provided through the touchscreen 19 or the user interface 22, after which the method 200 proceeds to 203 in which the heart model 1 is mapped onto the cardiac ultrasound image, e.g. a volumetric image, as previously explained. The cardiac ultrasound image including the overlaid heart model 1 in its mapping position determined in operation 203 is displayed in 205 on the display 18, such that the user can check whether the heart model 1 is correctly mapped onto the cardiac ultrasound image. This check is symbolized by operation 207 in which the processor arrangement 16 checks whether the user has provided a user touch instruction through the touchscreen 19 indicative of a misalignment of the heart model 1 with the cardiac ultrasound image.

For example, the user may provide an interruption instruction indicative of a misalignment of the heart model 1 with the cardiac ultrasound image, e.g. by tapping the touchscreen 19, which halts the automated processing and in particular the segmentation of the cardiac ultrasound image until the user has provided a mapping adjustment instruction through the touchscreen 19 in 209, which mapping adjustment instruction is interpreted by the processor arrangement 16 in 211 and used to remap the heart model 1 onto the cardiac ultrasound image accordingly. Typically, the gestures provided through the touchscreen 19 are interpreted and implemented by the processor arrangement 16 to operate on the spatial surface information of the mesh of the heart model 1 as displayed on the display 18. For example, the processor arrangement 16 may periodically check if a user command has been provided through the touchscreen 19, e.g. at a defined sampling rate, which in case such a user command is detected, this command is immediately interpreted and applied as a transformation onto the mesh, after which the method 200 reverts back to 205 in which the remapped heart model 1 is displayed as an overlay over the cardiac ultrasound image on the display 18 for acknowledgement by the user in 207 as previously explained.

In the following, a number of example types of user commands will be explained in further detail, which each type of user touch motion being associated with a different type of alteration of the mapping of the model 1. It should be understood that the example commands are not exhaustive and that other commands to invoke other operations, e.g. manipulations, of an anatomical model such as the heart model 1 may be contemplated. Equally, different types of touch interactions to the interactions explained below may be used to invoke such operations, as will be readily understood by the skilled person.

Figure 6:
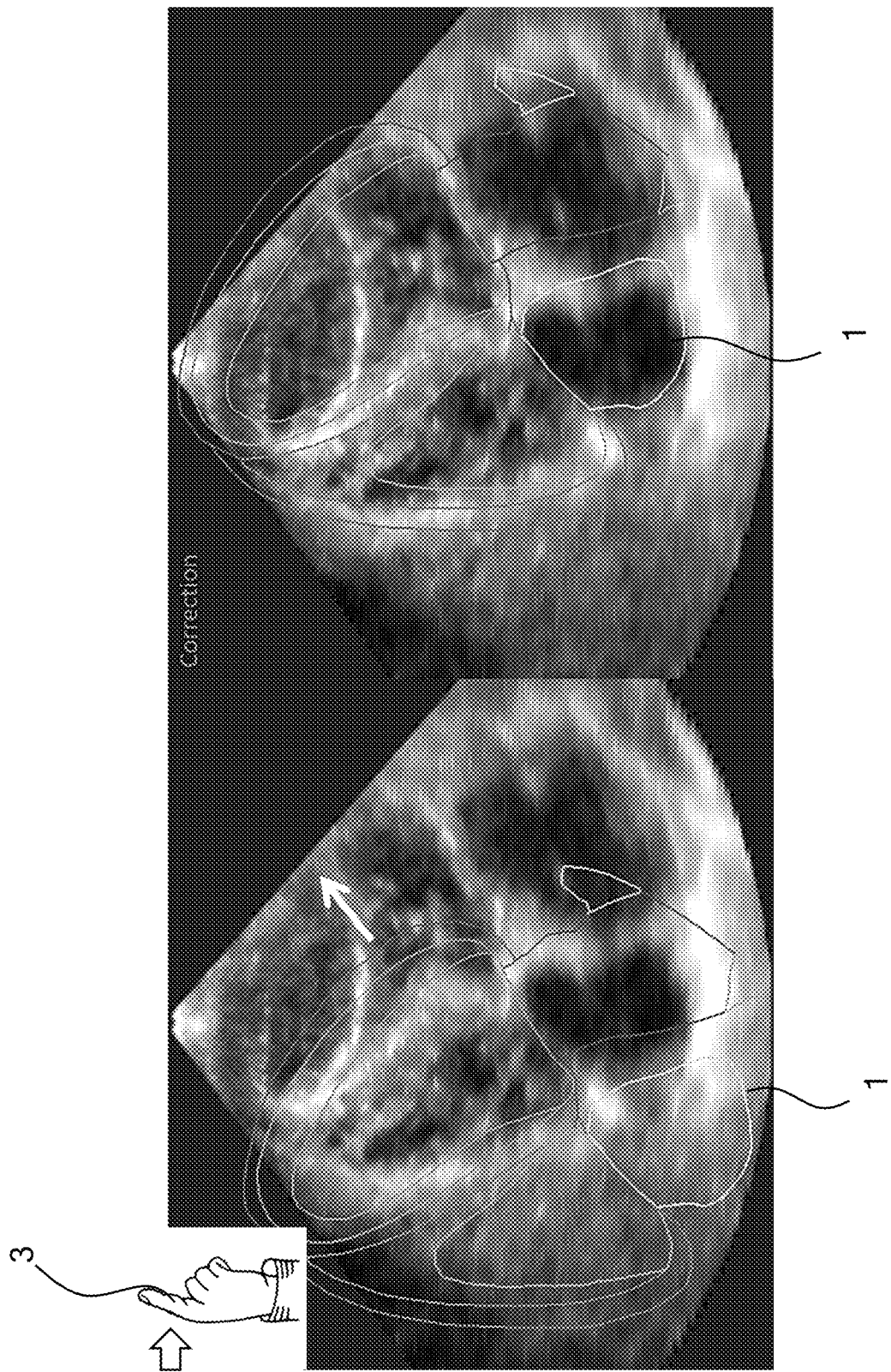
FIG. 6-10 schematically depict various aspect of example embodiments of the present invention.

In an example embodiment, the user may provide a translation instruction 3 for the heart model 1 through the touchscreen 19 as schematically depicted in FIG. 6. The user may by way of non-limiting example slide one or more fingers in the desired translation direction of the heart model 1 parallel to the current viewing plane of the cardiac ultrasound image, with the processor arrangement 16 adapted to translate the distance and direction of the sliding motion across the touchscreen 19 into a translation distance and direction for the heart model 1 relative to the cardiac ultrasound image as indicated by the arrow in the left pane of FIG. 6. The right pane of FIG. 6 (labeled 'Correction') depicts the remapped heart model 1 in accordance with this user touch instruction as executed by the processor arrangement 16. The user may acknowledge in 207 that the remapped heart model 1 is now appropriately mapped onto the cardiac ultrasound image, for example by refraining from providing further touch instructions through the touchscreen 19 or by providing a user instruction, e.g. through the touchscreen 19 or through the user interface 22 indicative of this acknowledgement.

Figure 7:
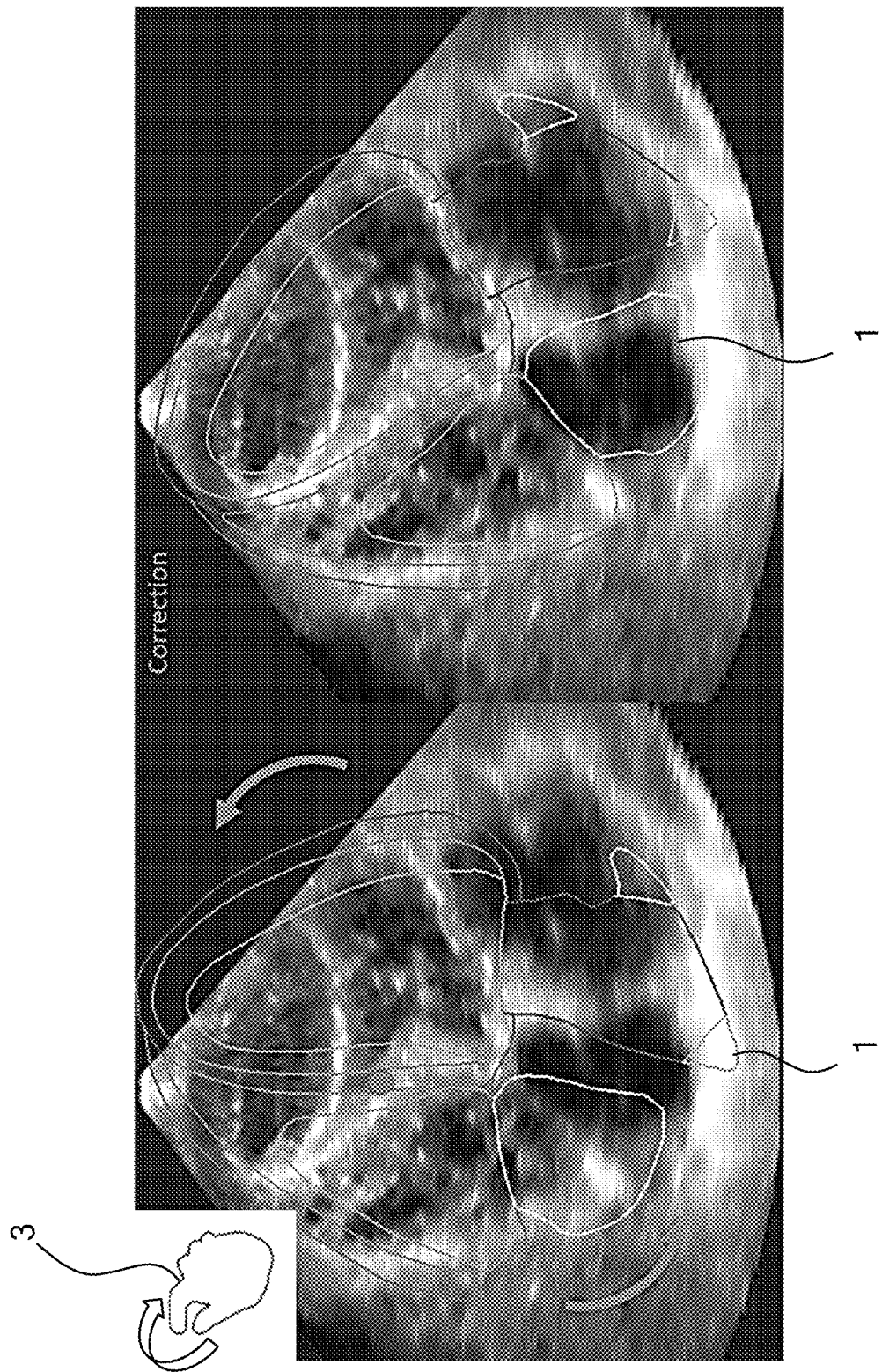

In another example embodiment, the user may provide a rotation instruction 3 for the heart model 1 through the touchscreen 19 as schematically depicted in FIG. 7. This may be used to correct rotational misalignment of the heart model 1 with the cardiac ultrasound image. To invoke such a rotational realignment of the heart model 1, the user may by way of non-limiting example make a turning motion on the touchscreen 19 with one or more fingers such as the thumb and the index finger, which turning motion is detected with the processor arrangement 16 and interpreted such that the degree (angle) of the turning motion provided by the user is translated into a degree (angle) of rotation of the heart model 1 in the direction of the turning motion around the normal vector axis of the current viewing plane of the cardiac ultrasound image as indicated by the curved arrows in FIG. 7, thereby yielding the rotated heart model 1 as depicted in the right pane of FIG. 7 (labeled 'Correction').

Figure 8:
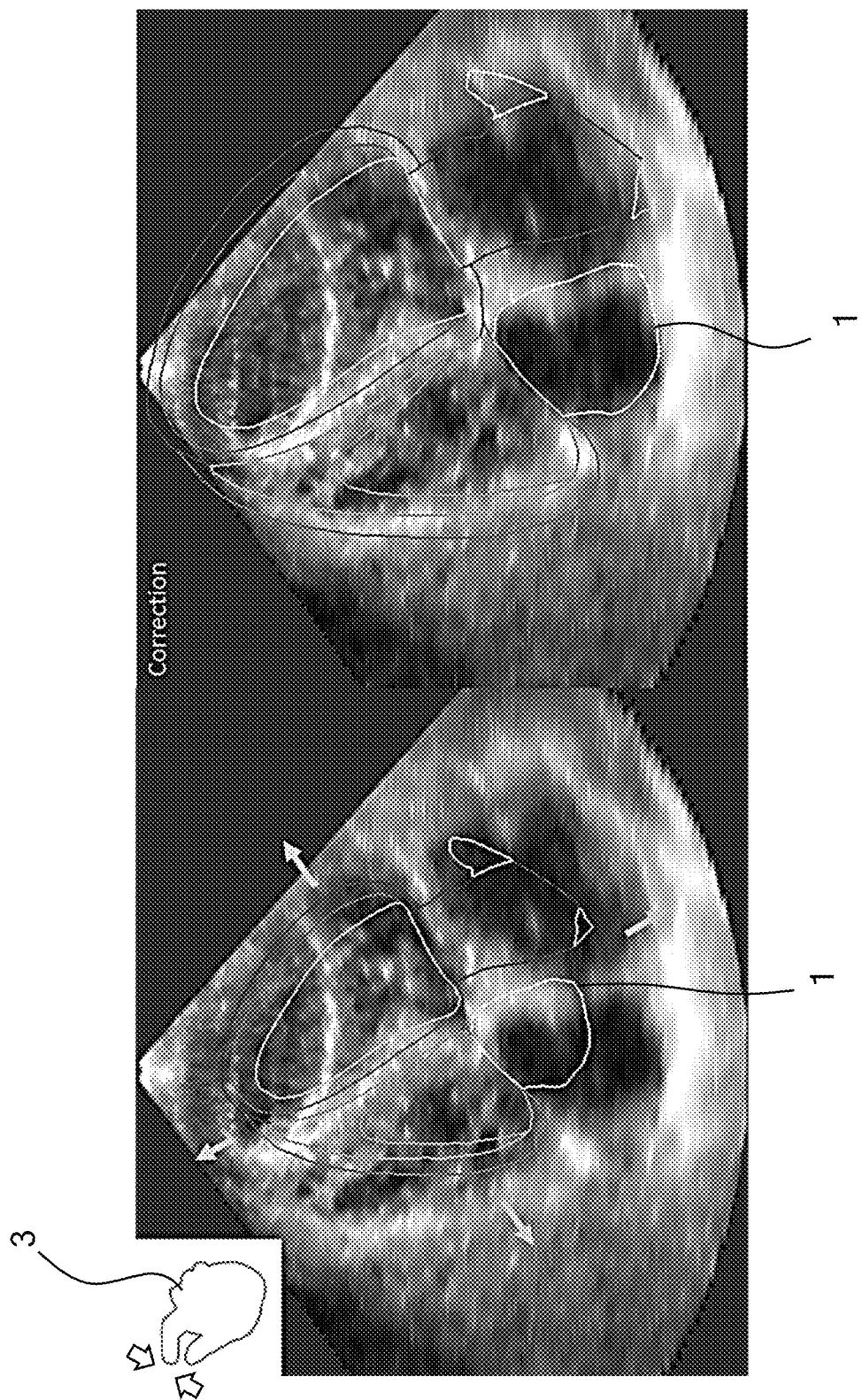

In another example embodiment, the user may provide a scaling instruction 3 for the heart model 1 through the touchscreen 19 as schematically depicted in FIG. 8. This may be used to correct and incorrect scaling of the heart model one relative to the cardiac ultrasound image, i.e. the cross-section of the heart visible in the cardiac ultrasound image. To invoke such a rescaling of the heart model 1, the user may by way of non-limiting example make a pinching motion with two or more fingers to reduce the size of the heart model 1 or a stretching motion with two fingers to increase the size of the heart model 1 on the touchscreen 19, e.g. using the thumb and index finger. The processor arrangement 16 as before is adapted to interpret such a scaling instruction received through the touchscreen 19 and rescale the heart model 1 in accordance with the received scaling instruction as indicated by the arrows in the left pane of FIG. 8, thereby resulting in the rescaled heart model 1' as depicted in the right pane of FIG. 8 (labeled 'Correction').

The extent of the scaling typically corresponds to the amount (distance) of pinching or stretching, e.g. between the fingers on the touchscreen 19, as will be readily understood by the skilled person.

Upon being established in operation 207 that the user acknowledges the mapping of the heart model 1 on the cardiac ultrasound image displayed on the display 18, the method 200 proceeds to 213 in which the cardiac ultrasound image is segmented by the processor arrangement 16 using any suitable segmentation algorithm as previously explained, after which the segmentation results are displayed on the display 18 in 215. Such segmentation results for example may include the measurement of dynamic cardiac parameters such as ejection fraction in order to enable the user to assess performance of the heart over a period of time, e.g. through one or more cardiac cycles.

Figure 9:
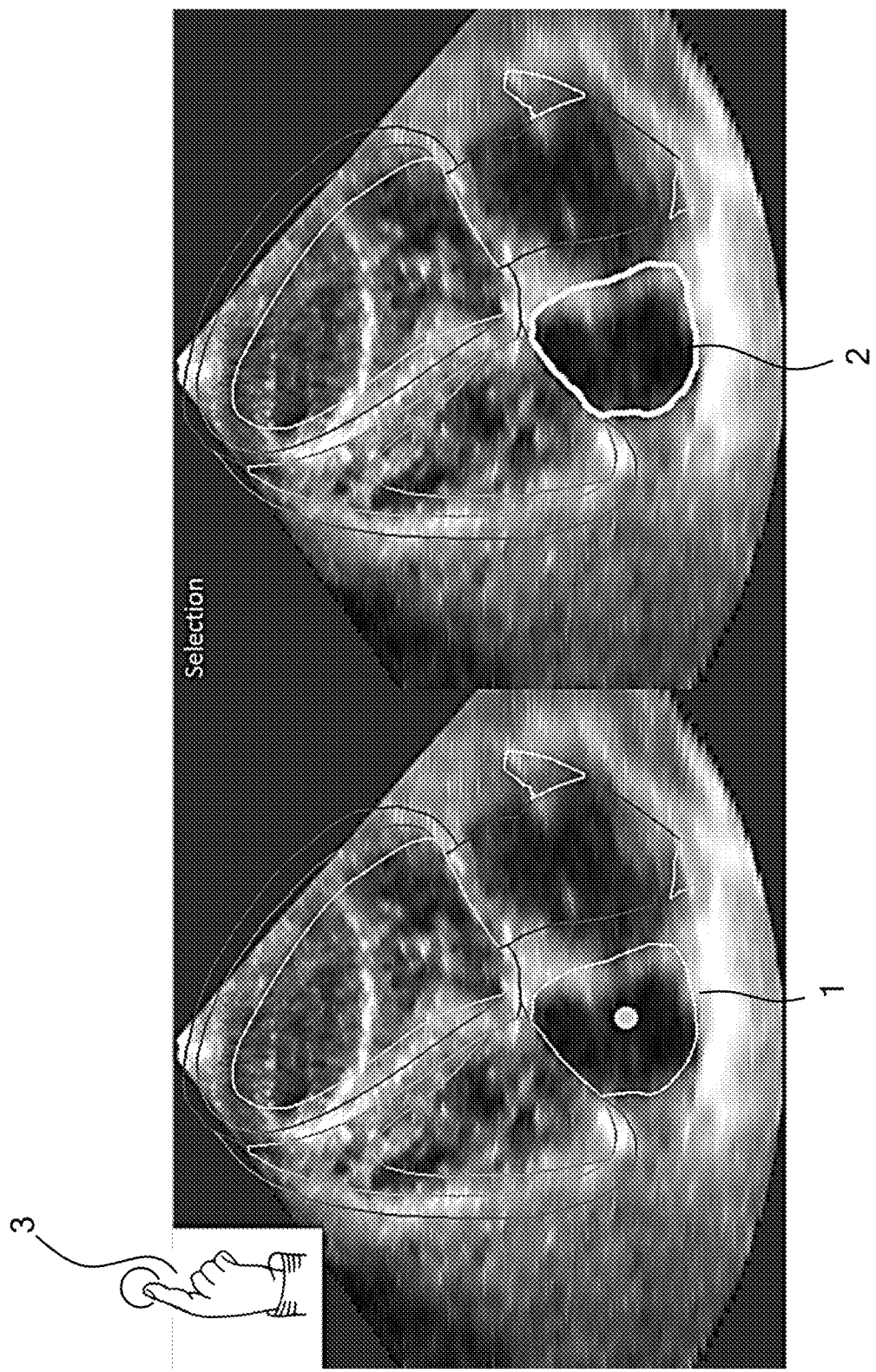

In an embodiment, the ultrasound image processing apparatus 10 is further adapted to allow a user to select a portion of the heart model 1 for selection or deselection of a particular anatomical component of the heart model. This is schematically depicted in FIG. 9. For example, the user may tap and hold an anatomical component 2 (here the left atrium model) of the heart model 1 for selection or deselection as indicated by the solid dot in the left pane of FIG. 9, for example to perform transformations or corrections of the heart model 1 using user touch instructions provided through the touchscreen 19 as previously explained at the component level, i.e. by facilitating such transformations or corrected for the selected component 2, which selection is schematically depicted in the right pane of FIG. 9 (labeled 'Selection'). The selected anatomical component 2 may be highlighted or otherwise emphasized on the display 18 in order to inform the user that the anatomical component 2 was successfully selected. Similarly, such highlighting or the like may be terminated upon successful deselection of the anatomical component 2. The mapping of the other parts of the heart model 1, e.g. the other anatomical components not selected, are typically frozen or fixated relative to the cardiac ultrasound image under investigation such that the user can selectively manipulate the selected anatomical component 2. This may involve the use of an influence radius that is either fixed or selectable using further touch gestures, as will be appreciated by the skilled person.

Figure 10:
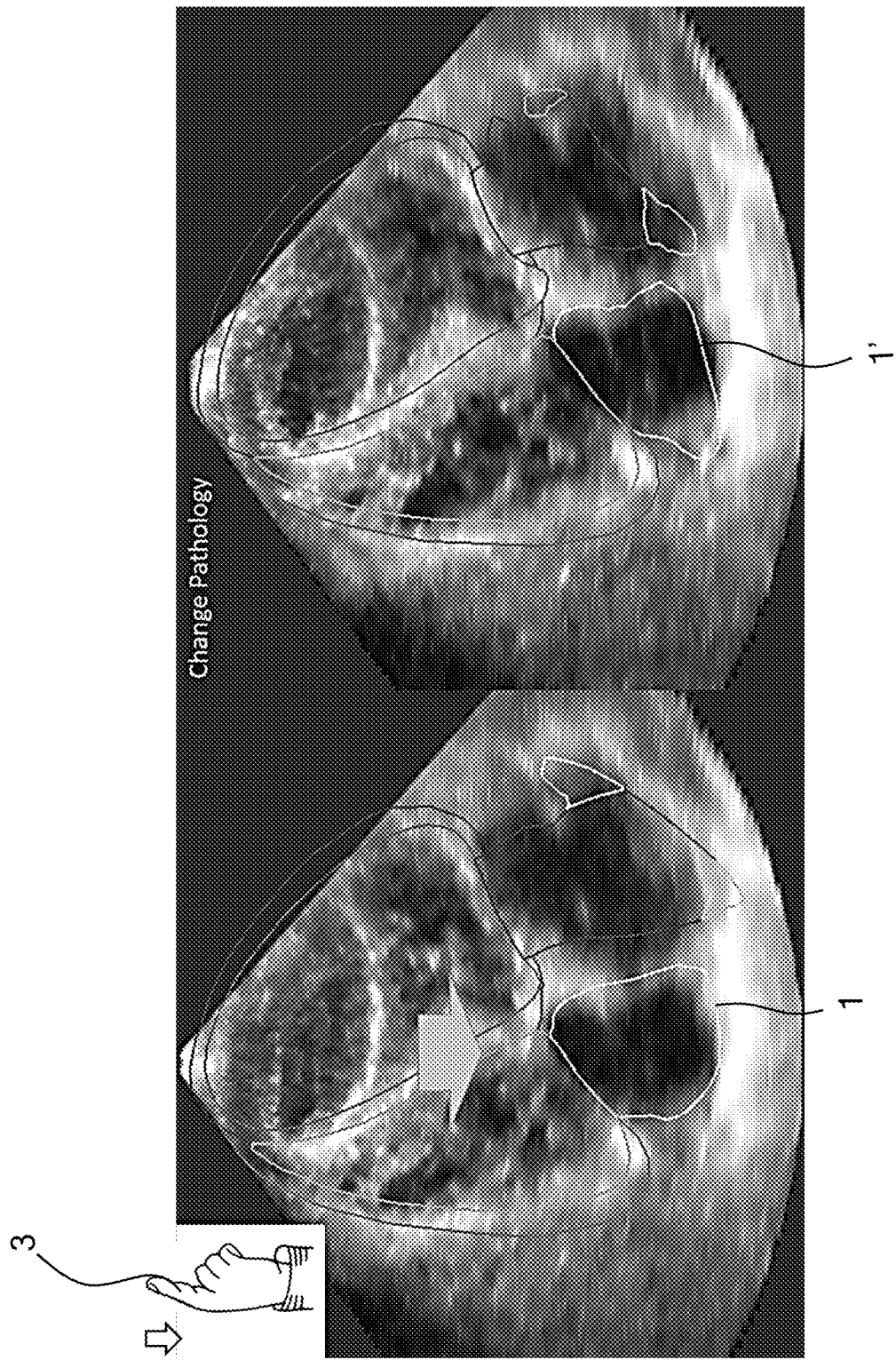

In another embodiment, the ultrasound image processing apparatus 10 is further adapted to allow a user to scroll through and select different initial modes or pathologies such as cardiac anatomies of special shape, e.g. dilation. This is schematically depicted in FIG. 10. For example, the user may make a swiping motion 3 on the touchscreen 19 to scroll through a library of different heart model shapes until arriving at the desired heart model 1', which may be selected any suitable manner, for example by terminating swiping action or by a tapping action on the desired heart model 1', thus leading to the selection of this heart model as depicted in the right pane of FIG. 10 (labeled 'Change Pathology').

It should be understood that any of the aforementioned user touch instructions provided through the touchscreen 19 may be provided at any point during the processing of the cardiac ultrasound image, e.g. during the mapping of the heart model 1 onto the cardiac ultrasound image and the subsequent segmenting of the cardiac ultrasound image according to the mapped heart model 1, such that variations to the flow of the method 200 are contemplated without departing from the teachings of the present invention.

Moreover, it should be understood that although embodiments of the present invention have been explained in the context of the mapping of a segmentation model onto a heart, the teachings of the present invention are equally applicable to any other ultrasound imaging application in which a segmentation model is to be mapped onto an anatomical feature of interest such as an internal organ of the patient 12, a fetus within a female patient 12, and so on.

According to an aspect of the present invention, a computer program product may be provided comprising a computer readable storage medium having computer readable program instructions (code) embodied therewith for, when executed on the processor arrangement 16 of the ultrasound image processing apparatus 10, cause the processor arrangement 16 to implement any embodiment of the method 200.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out the methods of the present invention by execution on the processor arrangement may be written in any combination of one or more programming languages, including an object oriented programming language such as Java, Smalltalk, C++ or the like and conventional procedural programming languages, such as the "C" programming language or similar programming languages. The program code may execute entirely on the processor arrangement as a stand-alone software package, e.g. an app, or may be executed partly on the processor arrangement and partly on a remote server. In the latter scenario, the remote server may be connected to the ultrasound image processing apparatus 10 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the processor arrangement of the ultrasound image processing apparatus 10, such that the instructions create means for implementing the functions/acts specified in the flowchart and/or block diagram block or blocks. These computer program instructions may also be stored in a computer-readable medium that can direct the ultrasound image processing apparatus 10 to function in a particular manner.

The computer program instructions may be loaded onto the processor arrangement to cause a series of operational steps to be performed on the processor arrangement, to produce a computer-implemented process such that the instructions which execute on the processor arrangement provide processes for implementing the functions/acts specified in the flowchart and/or block diagram block or blocks. The computer program product may form part of the ultrasound image processing apparatus 10, e.g. may be installed on the ultrasound image processing apparatus 10.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound image processing apparatus comprising:
a processor arrangement configured to map a model of an anatomical feature of interest onto an ultrasound image showing at least a section of the anatomical feature of interest and to perform automatic segmentation of the ultrasound image in accordance with the mapped model; and
a touchscreen display configured to display the ultrasound image and the mapping of the model overlaid on the ultrasound image;
wherein the processor arrangement is configured to recognize a type of user touch motion, applied by a user directly to the mapping of the model on the touchscreen display to manipulate the mapping of the model in relation to the ultrasound image, from a plurality of defined types of user touch motion, each type of user touch motion being associated with a particular type of alteration of the mapping of the model onto the ultrasound image, and to alter the mapping of the model onto the ultrasound image in accordance with the recognized type of user touch motion;
wherein the processor arrangement is configured to continue to perform the automatic segmentation of the ultrasound image in accordance with the altered mapping of the model onto the ultrasound image.

2. The ultrasound image processing apparatus of claim 1, wherein the model comprises a plurality of anatomical components, and wherein the processor arrangement is configured to select an anatomical component of the plurality of anatomical components in response to a user interaction by the user with a region of the touchscreen display displaying the selected anatomical component.

3. The ultrasound image processing apparatus of claim 2, wherein the processor arrangement is further configured to further alter the mapping of the model onto the ultrasound image by altering mapping of the selected anatomical component in response to a further user touch motion provided through the touchscreen display.

4. The ultrasound image processing apparatus of claim 1, wherein the model is configurable, and wherein the processor arrangement is configured to select a configuration of the model in response to a swiping motion provided by the user on the touchscreen display.

5. The ultrasound image processing apparatus of claim 1, wherein the ultrasound image processing apparatus is a workstation or a portable ultrasound image processing apparatus.

6. An ultrasound imaging system comprising:
an ultrasound probe for acquiring an ultrasound image of an anatomical feature of interest;
a processor arrangement configured to receive the ultrasound image;
a touchscreen display configured to display at least the ultrasound image; and
a memory configured to store computer program instructions that, when executed by the processor arrangement, cause the processor arrangement to:
map a model of the anatomical feature of interest onto the ultrasound image showing at least a section of the anatomical feature of interest, wherein the touchscreen display displays the mapping of the model overlaid on the ultrasound image;
recognize a type of user touch motion, applied by a user directly to the mapping of the model on the touchscreen display to manipulate the mapping of the model relative to the ultrasound image, from a plurality of defined types of user touch motion, each type of user touch motion being associated with a particular type of alteration of the mapping of the model onto the ultrasound image;
alter the mapping of the model onto the ultrasound image in accordance with the recognized type of user touch motion; and
segment the ultrasound image in accordance with the altered mapping of the model onto the ultrasound image.

7. A computer-implemented method of extracting parametric measurements from an ultrasound image showing at least a section of an anatomical feature of interest of a patient, the method comprising:
mapping a model of the anatomical feature of interest onto the ultrasound image;
displaying the ultrasound image and the mapping of the model overlaid on the ultrasound image on a touchscreen display;
receiving a user touch motion from the touchscreen display;
recognizing a type of the user touch motion, applied by a user directly to the mapping of the model on the touchscreen display to manipulate the mapping of the model relative to the ultrasound image, from a plurality of types of user touch motions, each type of user touch motion being associated with a particular type of alteration of the mapping of the model;
altering the mapping of the model in accordance with the recognized type of the user touch motion to provide an altered map model; and
segmenting the ultrasound image in accordance with the altered mapped model to extract the parametric measurements.

8. The computer-implemented method of claim 7, further comprising displaying the extracted parametric measurements on the touchscreen display.

9. The computer-implemented method of claim 7, wherein the model comprises a plurality of anatomical components, and wherein the method further comprises:
selecting an anatomical component of the plurality of anatomical components in response to a user interaction with a region of the touchscreen display displaying the selected anatomical component.

10. The computer-implemented method of claim 9, further comprising:
altering the mapping of the selected anatomical component in response to a further user touch instruction provided through the touchscreen display.

11. The computer-implemented method of claim 7, wherein the model is configurable, and wherein the method further comprises:
selecting a configuration of the model in response to a swiping motion provided by the user on the touchscreen display.

12. The ultrasound image processing apparatus of claim 1, wherein the type of user touch motion comprises a translation motion involving the user sliding one or more fingers across the touchscreen display in a desired translation direction of the model.

13. The ultrasound image processing apparatus of claim 1, wherein the type of user touch motion comprises a rotation motion involving the user turning at least two fingers on the touchscreen display in a desired rotation direction of the model.

14. The ultrasound image processing apparatus of claim 1, wherein the type of user touch motion comprises a scaling motion involving the user making pinching motion or a stretching motion with at least two fingers on the touchscreen display to decrease or increase a desired scale of the model, respectively.

15. The ultrasound imaging system of claim 6, further comprising:
a display configured to display the ultrasound image with the altered mapping.

16. The ultrasound imaging system of claim 6, wherein the model comprises a plurality of anatomical components, and wherein the instructions further cause the processor arrangement to select an anatomical component of the plurality of anatomical components in response to a user interaction by the user with a region of the touchscreen display displaying the selected anatomical component.

17. The ultrasound imaging system of claim 16, wherein the instructions further cause the processor arrangement to further alter the mapping of the model onto the ultrasound image by altering mapping of the selected anatomical component in response to a further user touch motion provided through the touchscreen display.

18. The ultrasound imaging system of claim 6, wherein the model is configurable, and wherein the instructions further cause the processor arrangement to select a configuration of the model in response to a swiping motion provided by the user on the touchscreen display.

\* \* \* \* \*